(12) United States Patent
Faccini et al.

(10) Patent No.: US 7,903,250 B1
(45) Date of Patent: Mar. 8, 2011

(54) CONTROL BY SAMPLE REFLECTIVITY

(75) Inventors: Fabio A. Faccini, San Jose, CA (US);
Torsten R. Kaack, Los Altos, CA (US);
Jiyou Fu, Sunnyvale, CA (US);
Zhiming Jiang, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 176 days.

(21) Appl. No.: 12/477,571

(22) Filed: Jun. 3, 2009

Related U.S. Application Data

(60) Provisional application No. 61/059,888, filed on Jun. 9, 2008.

(51) Int. Cl.
*G01N 21/55* (2006.01)

(52) U.S. Cl. .......................... 356/445; 356/448

(58) Field of Classification Search .......... 356/445–448, 356/450–458
See application file for complete search history.

(56) References Cited

U.S. PATENT DOCUMENTS

| 4,377,340 | A  | * | 3/1983 | Green et al. ............... 356/237.3 |
| 6,507,393 | B2 | * | 1/2003 | Batchelder ................ 356/237.1 |
| 6,693,293 | B2 | * | 2/2004 | Oomori et al. ............. 250/559.4 |
| 6,895,360 | B2 | * | 5/2005 | Liu et al. ....................... 702/172 |
| 7,372,557 | B2 | * | 5/2008 | Oomori et al. ............. 356/237.1 |
| 7,659,976 | B2 | * | 2/2010 | Kaller et al. ............... 356/239.2 |

* cited by examiner

*Primary Examiner* — Gregory J Toatley
*Assistant Examiner* — Jarreas C Underwood
(74) *Attorney, Agent, or Firm* — Luedeka, Neely & Graham, P.C.

(57) ABSTRACT

A method of performing an investigation of a substrate, by measuring a reflectivity of the substrate, comparing the reflectivity of the substrate to an anticipated reflectivity value, selectively subjecting the substrate to a laser beam for a predetermined duration and at a predetermined energy only when the reflectivity of the substrate is within a specified tolerance of the anticipated reflectivity value, selectively signaling a fault condition when the reflectivity of the substrate is not within the specified tolerance of the anticipated reflectivity value, and selectively performing the investigation of the substrate only when the reflectivity of the substrate is within the specified tolerance of the anticipated reflectivity value.

12 Claims, 1 Drawing Sheet

CONTROL BY SAMPLE REFLECTIVITY

This application claims all rights and priority on U.S. provisional application 61/059,888 filed 2008, Jun. 9. This invention relates to the field of integrated circuit fabrication. More particularly, this invention relates to preventing damage to integrated circuits during investigation processes.

FIELD

Background

During integrated circuit fabrication processes, the integrated circuits typically receive a variety of different surface inspections and measurements, such as optical inspections and measurements. As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

The term "tool" as used herein generally refers to inspection or measurement systems used in the integrated circuit fabrication industry. The term "investigation" as used herein generally refers to the process of inspection or measurement as used in the integrated circuit fabrication industry. As used herein, the term "substrate" refers to the substrates on which the integrated circuits are fabricated, the masks or reticles from which the patterns used to form the integrated circuits are transferred, and other types of substrates as used in the integrated circuit fabrication industry.

Substrates often absorb or otherwise accumulate on their surfaces different types of airborne molecular contamination during the fabrication process—generally referred to as contaminants herein. These contaminants are typically removed in a variety of ways, depending upon the process to next be performed on the substrate.

For example, prior to an investigation, the substrate may be subjected to a laser pulse in the spot on the substrate to be investigated. This laser pulse tends to vaporize the contaminants so that the investigation of the substrate by the tool is not deleteriously effected by the contaminants. In some instances, the laser and controller are integrated with the tool, making the use of the laser very convenient during the investigation process.

However, subjecting the substrate to improper conditioning by the laser, such as too high an energy or for too long a time, can damage the substrate. Alternately, processing the substrate with too low an energy or for too short a time might result in the contaminants remaining on the substrate and affecting the results of the investigation.

What is needed, therefore, is a system that overcomes problems such as those described above, at least in part.

SUMMARY

The above and other needs are met by a method of performing an investigation of a substrate, by measuring a reflectivity of the substrate, comparing the reflectivity of the substrate to an anticipated reflectivity value, selectively subjecting the substrate to a laser beam for a predetermined duration and at a predetermined energy only when the reflectivity of the substrate is within a specified tolerance of the anticipated reflectivity value, selectively signaling a fault condition when the reflectivity of the substrate is not within the specified tolerance of the anticipated reflectivity value, and selectively performing the investigation of the substrate only when the reflectivity of the substrate is within the specified tolerance of the anticipated reflectivity value.

Thus, the embodiments of the present invention identify and define a correlation between the reflectivity of the substrate and the desired power to be delivered by the laser to the surface of the substrate. In this manner, trivial errors such as investigating a substrate with the wrong recipe—which would either not remove the contaminants or which would damage the substrate—are avoided.

In various embodiments according to this aspect of the invention, at least one of the predetermined energy and the predetermined duration are modified based on a magnitude of variance between the reflectivity of the substrate and the anticipated reflectivity value. In some embodiments the investigation is a measurement of the substrate and in other embodiments the investigation is an inspection of the substrate. In some embodiments the predetermined duration and the predetermined energy are sufficient to remove contaminants from the substrate without damaging the substrate.

According to another aspect of the invention there is described a tool for performing an investigation of a substrate. A controller controls the operation of the tool. A stage receives the substrate and provides motion to the substrate under the control of the controller. A sensor measures the reflectivity of the substrate, and the controller compares the reflectivity of the substrate to a programmed value, and then determines a variance. When the variance does not exceed a limit, a laser conditions the substrate at an energy and a duration under the control of the controller. A tool head performs the investigation of the substrate.

In various embodiments according to this aspect of the invention, at least one of the energy and the duration are modified based on a magnitude of the variance. The investigation in some embodiments is a measurement of the substrate, and in other embodiments is an inspection of the substrate. In some embodiments the duration and the energy are sufficient to remove contaminants from the substrate without damaging the substrate.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
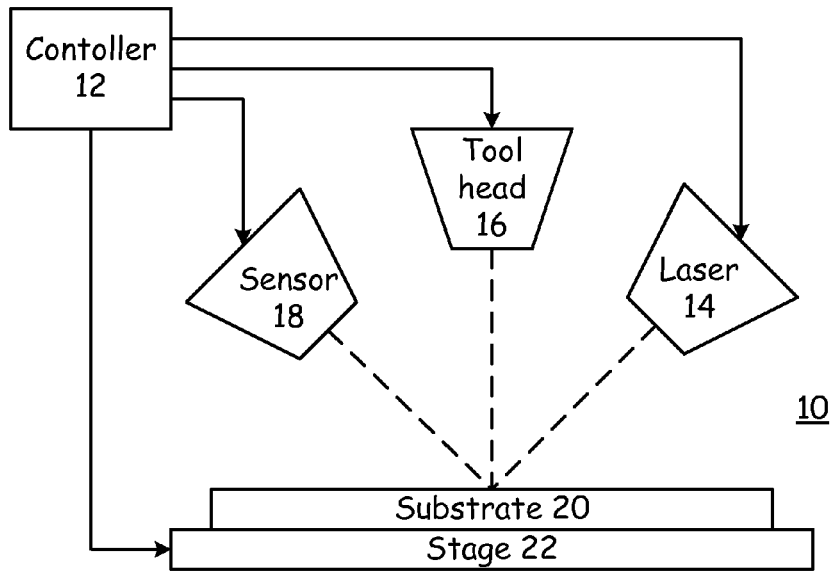
FIG. 1 is a functional block diagram of an investigation tool according to an embodiment of the present invention.

With reference now to FIG. 1, there is depicted a functional block diagram of a tool 10 according to an embodiment of the present invention. The tool 10 is controlled by a controller 12, which communicates with the other components of the tool 10. A tool head 16 takes the measurements on the substrate 20 or makes the inspection of the substrate 20. The laser 14 prepares the substrate 20 prior to the investigation, as described elsewhere herein. The stage 22 holds the substrate 20 and provides motion for the substrate 20 relative to the tool head 16, such as rotational, elevational, and translational movement. The sensor 18 takes a measurement of the substrate 20, so as to provide information for the proper operation of the laser 14, as described in more detail hereafter. The controller 12 receives information from and sends commands to the various components of the tool 10.

Figure 2:
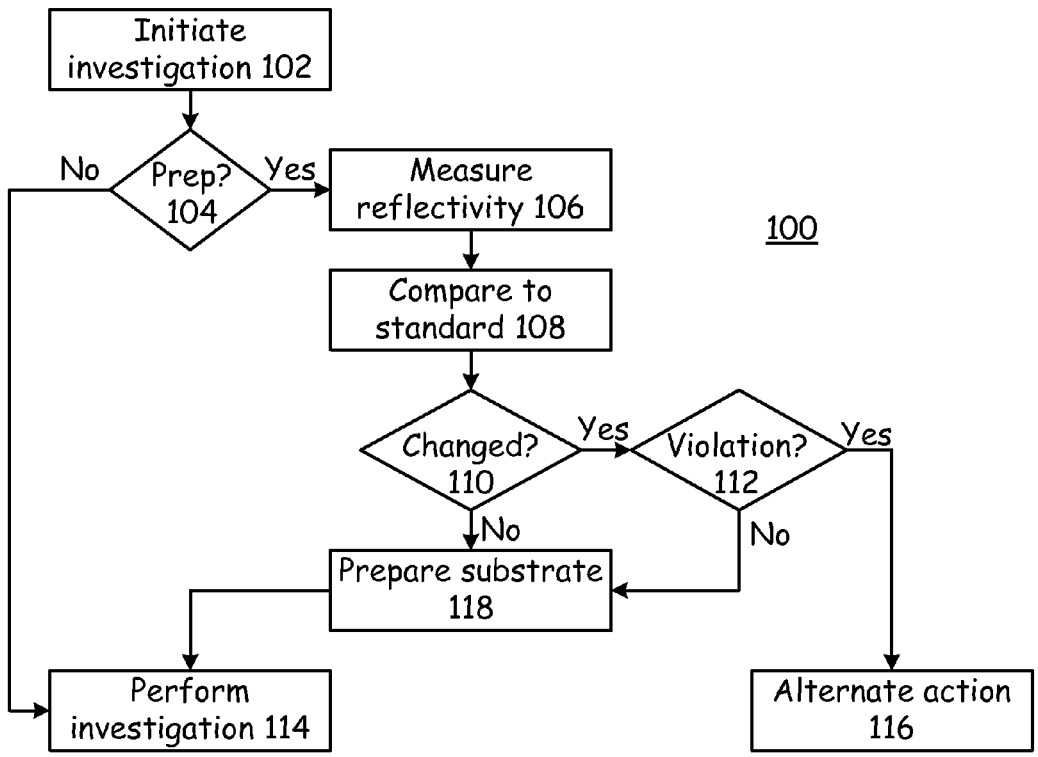
FIG. 2 is a flow chart of a method according to an embodiment of the present invention.

With reference now to FIG. 2 there is depicted a flow chart for a method 100 for the operation of the tool 10 according to an embodiment of the invention. The first step is to initiate the investigation of the substrate 20 with the tool 10, as given in block 102. This is accomplished by initiating a start command through the controller 12, which can be done, for example, by entering a command on an attached keyboard, using a touch screen monitor, or sending a command remotely through a network interface.

The investigation in some embodiments proceeds according to a selected program or recipe within the controller 12. The recipe specifies a specific investigation to be performed on a specific substrate 20 type. One step of the recipe is the determination as to whether the substrate 20 will receive a preparatory processing prior to the investigation, as given in block 104. The preparatory processing is performed by irradiating the substrate 20 at a desired investigation location with a beam produced by the laser 14, as given in block 118 and described below. However, as mentioned above, there can be problems associated with the laser 14 being operated at too high or too low an energy, or for too long or too short a time. If no preparatory processing 118 is to be given to the substrate 20, then the method continues by performing the desired investigation, as given in block 114.

If preparatory processing 118 is desired, then the controller 12 instructs the sensor 18 to provide a reflectivity measurement of the substrate 20, as given in block 106. In such an embodiment, the sensor 18 represents all of the components necessary to take a reflectivity measurement. The reflectivity measurement can be taken in a number of different ways, such as with a reflectometer, ellipsometer, or other methods.

The controller 12 evaluates the reflectivity measurement in view of the recipe that has been selected for the substrate 20. This evaluation includes comparing the reflectivity measurement to a standard value, as given in block 108. The standard value is in one embodiment a theoretical value derived from the film stack information associated with the selected recipe. This information can be factory predetermined and coded into the tool 10 so that users cannot override it. Alternately, the standard value represents an actual value that has been read for a similar substrate 20 that the recipe was designed to process. Further, the standard value can be something that an engineer has programmed into the tool 10.

If the reflectivity measurement varies from the standard value that is programmed into the recipe, as determined in block 110, then it is an indication that some unexpected condition exists in regard to the substrate 20. For example, the wrong type of substrate 20 might be loaded in the tool 10—or said another way—the wrong recipe for the substrate 20 might have been selected. Another possibility is that the substrate 20 has a condition that bears additional investigation prior to the desired processing and investigation by the tool 10.

However, if no discrepancy between the anticipated reflectivity measurement and the actual reflectivity measurement exists, as determined in block 110, then the preparatory processing 118 is performed. During step 118, the laser 14 is fired with an energy and duration as specified by the recipe, under the control of the controller 12. The specified energy and duration is selected to provide sufficient energy to adequately remove the contaminants from the specific substrate 20 type as designated by the recipe, without damaging the specific substrate 20 type. This kind of information can be determined by engineering investigation, and programmed into the recipe prior to production release of the tool 10.

After the preparatory processing 118 of the substrate 20, the desired investigation of the substrate 20 is performed, as given in block 114. It is appreciated that the steps of preparing the substrate 118 and performing the investigation 114 can be performed multiple times on a given spot of the substrate 20, and that the substrate 20 can be moved, such as by the stage 22, between multiple preparations 118 and investigations 114 of the same substrate 20, all under the control of the controller 12, as specified by the recipe.

If a discrepancy is determined between the measured reflectivity and the anticipated reflectivity, as determined in block 110, then the magnitude of the discrepancy is evaluated as given in block 112, to determine whether a violation exists. For example, if the magnitude of the discrepancy is within a predetermined range as programmed into the recipe, then the laser conditioning 118 and the investigation 114 can still be performed.

In various embodiments, the violation can be determined based upon a calculation that is performed, such as on the average reflectivity measurements for prior substrates 20 that had been processed using the same recipe, plus or minus some amount of variance, such a given number of standard deviations. Alternately, the violation can be determined with an absolute value that is programmed into the controller 12 for the given recipe.

In some embodiments, if the magnitude of the discrepancy does not produce a violation, then the magnitude of the discrepancy is used to temporarily adjust at least one of the programmed energy and time parameters for the beam that is produced by the laser 14. For example, a reflectivity measurement that is slightly higher than the standard as determined in block 110, but does not violate the acceptable range of measurements as given in block 112, can in some embodiments be compensated for by adjusting at least one of the energy and duration of the beam from the laser 14 during the preparation 118 of the substrate 20. Such modifications of the laser 14 parameters as dictated by the recipe are under the control of the controller 12. However, in some embodiments these modifications are temporary and are only used for the specific substrate 20 that produced them.

The magnitude of the modifications to the laser 14 as described above can be derived from various sources, including calibration curves, previous characterizations, theoretical laser 14 response models, and other means. A simple way to compensate for delivered power is by use of corrections proportional to the reflectivity changes, such as $P=[1-R_0]P_0/[1-R]$, where the 0 subscript refers to nominal conditions, P is power and R is reflectivity. A higher order equation could also be used to describe the relationship between reflectivity change and laser 14 parameters.

If the magnitude of the discrepancy is greater than the predetermined range as programmed into the recipe as determined in block 112, then some alternate action 116 is performed. This alternate action could be to stop the investigation and provide a signal or warning of some type, such as on a display of the controller 12, or through a network connected to the controller 12.

Thus, the present invention identifies and defines a correlation between the reflectivity of the substrate 20 and the power delivered by the laser 14 to the surface of the substrate 20. In this manner, trivial errors such as investigating a substrate 20 with the wrong recipe are avoided.

The methods described herein can be applied to various wavelengths of lasers 14 and to multiple lasers 14 operating simultaneously, selectively, or serially. Further, these methods can be applied to substrate power delivery systems other than lasers 14, such as other high intensity light sources such as a flash lamp or an arc lamp.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of performing an investigation of a substrate, the method comprising the sequential steps of:
   measuring a reflectivity of the substrate,
   comparing the reflectivity of the substrate to an anticipated reflectivity value,
   selectively conditioning the substrate with a light source for a predetermined duration and at a predetermined energy only when the reflectivity of the substrate is within a specified tolerance of the anticipated reflectivity value,
   selectively signaling a fault condition when the reflectivity of the substrate is not within the specified tolerance of the anticipated reflectivity value, and
   selectively performing the investigation of the substrate only when the reflectivity of the substrate is within the specified tolerance of the anticipated reflectivity value.

2. The method of claim 1, wherein the light source is at least one of a laser, a flash lamp, and an arc lamp.

3. The method of claim 1, wherein at least one of the predetermined energy and the predetermined duration are modified based on a magnitude of variance between the reflectivity of the substrate and the anticipated reflectivity value.

4. The method of claim 1, wherein the investigation is a measurement of the substrate.

5. The method of claim 1, wherein the investigation is an inspection of the substrate.

6. The method of claim 1, wherein the predetermined duration and the predetermined energy are sufficient to remove contaminants from the substrate without damaging the substrate.

7. A tool for performing an investigation of a substrate, the tool comprising:
   a controller for controlling operation of the tool,
   a stage for receiving the substrate and for providing motion to the substrate under control of the controller,
   a sensor for measuring a reflectivity of the substrate,
   the controller for comparing the reflectivity of the substrate to a programmed value and determining a variance,
   a light source for conditioning the substrate at an energy and a duration under control of the controller and only when the variance does not exceed a limit, and
   a tool head for performing the investigation of the substrate.

8. The tool of claim 7, wherein the light source is at least one of a laser, a flash lamp, and an arc lamp.

9. The tool of claim 7, wherein at least one of the energy and the duration are modified by the controller based on a magnitude of the variance.

10. The tool of claim 7, wherein the investigation is a measurement of the substrate.

11. The tool of claim 7, wherein the investigation is an inspection of the substrate.

12. The tool of claim 7, wherein the duration and the energy are sufficient to remove contaminants from the substrate without damaging the substrate.

* * * * *